United States Patent

Wiehe et al.

[11] Patent Number: 6,048,904
[45] Date of Patent: Apr. 11, 2000

[54] BRANCHED ALKYL-AROMATIC SULFONIC ACID DISPERSANTS FOR SOLUBLIZING ASPHALTENES IN PETROLEUM OILS

[75] Inventors: Irwin A. Wiehe, Gladstone; Ramesh Varadaraj, Flemington; Torris G. Jermansen, Far Hills; Raymond J. Kennedy, Hampton; Cornelius H. Brons, Washington, all of N.J.

[73] Assignee: Exxon Research and Engineering Co., Florham Park, N.J.

[21] Appl. No.: 09/203,141

[22] Filed: Dec. 1, 1998

[51] Int. Cl.$^7$ .............................. C07C 7/20; C07C 303/02
[52] U.S. Cl. .................... 516/20; 516/909; 562/45; 562/88; 562/91; 106/278; 208/48 AA; 208/265; 208/282
[58] Field of Search ................. 516/20, 909; 562/45, 562/88, 91; 106/278; 208/48 AA, 265, 282

[56] References Cited

U.S. PATENT DOCUMENTS

| | | | |
|---|---|---|---|
| 3,234,297 | 2/1966 | Cohen | 562/45 |
| 4,873,025 | 10/1989 | Bolsman | 562/91 |
| 5,186,846 | 2/1993 | Brueckmann et al. | 562/91 |
| 5,202,056 | 4/1993 | Sung et al. | 44/280 |
| 5,207,802 | 5/1993 | Baumann | 516/20 |
| 5,596,128 | 1/1997 | Ogata et al. | 562/91 |

*Primary Examiner*—Jacqueline V. Howard
*Attorney, Agent, or Firm*—Ronald D. Hantman

[57] ABSTRACT

The present invention is an asphaltene dispersant containing an aromatic, a sulfonic acid head, and an alkyl tail containing 16 carbons or more and at least one branch of a methyl or longer alkyl. Preferably, the aromatic is a fused two ring aromatic and the tail is a two, branched alkyl tail of 30 carbons or longer.

7 Claims, 1 Drawing Sheet

Structure of Iso-C$_{15}$-C$_{15}$ Naphthalene Sulfonic Acid

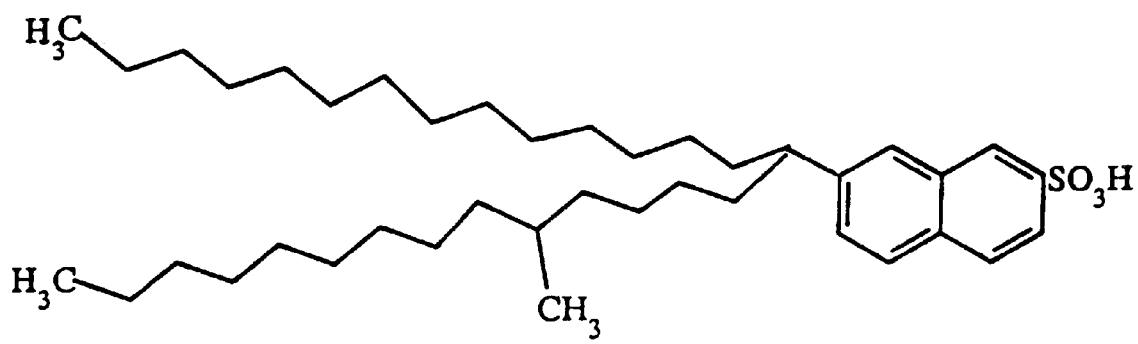
Figure 1. Structure of Iso-$C_{15}$-$C_{15}$ Naphthalene Sulfonic Acid
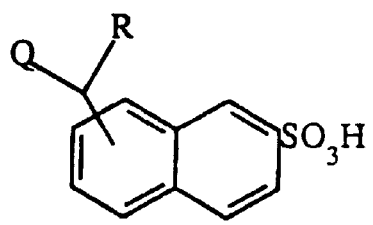
$R + Q \geq 29$
where R & Q are alkyl chains with at least one branched methyl or longer alkyl group for every 20 carbons
Figure 2. Preferred Asphaltene Dispersant Structure

BRANCHED ALKYL-AROMATIC SULFONIC ACID DISPERSANTS FOR SOLUBLIZING ASPHALTENES IN PETROLEUM OILS

BACKGROUND OF THE INVENTION

The present invention relates to an additive that when blended with petroleum oils in low concentration, the tendency of the oil to foul and coke surfaces is reduced. This is achieved by increasing the solvency of the asphaltenes, the least soluble fraction, in the petroleum oil.

It is well known that petroleum crude oils and asphaltene containing oils derived from petroleum crude oils have the tendency to deposit organic solids, called foulant and coke, on refinery process equipment that contact the oil. Such process equipment include, but are not limited to, pipes, tanks, heat exchangers, furnace tubes, fractionators, and reactors. Even small amounts of foulant or coke results in large energy loss because of much poorer heat transfer through foulant and coke as opposed to metal walls alone. Moderate amounts of foulant and coke cause high pressure drops and interfere with and make process equipment operate inefficiently. Finally, large amounts of foulant or coke plug up process equipment to prevent flow or otherwise make operation intolerable, requiring the equipment to be shut down and cleaned of foulant and coke.

It is also well known that petroleum derived, asphaltene containing oils that have undergone reaction at high temperatures, above 350° C., have a tendency for rapidly fouling process equipment, either on cooling or by blending with a more paraffinic oil. Such processed oils include, but are not limited by, the highest boiling distillation fraction after thermally or catalytically hydrothermally converting atmospheric or vacuum resid of petroleum crude and the highest boiling fraction of the liquid product of fluid catalytic cracking, called cat cracker bottoms or cat slurry oil or decant oil. This rapid fouling is caused by asphaltenes that become insoluble on cooling or on blending with a more paraffinic oil. Here asphaltenes are defined as the fraction of the oil that is soluble when the oil is blended with 40 volumes of toluene but insoluble when the oil is blended with 40 volumes of n-heptane. If the asphaltenes become insoluble at high temperatures, above 350° C., they rapidly form toluene insoluble coke (see I. A. Wiehe, Industrial & Engineering Chemistry Research, Vol. 32, 2447–2454). However, it is not well known that the mere blending of two or more unprocessed petroleum crude oils can cause the precipitation of insoluble asphaltenes that can rapidly foul process equipment or when such crude oil blends are rapidly heated above 350° C., the insoluble asphaltenes can coke pipestill furnace tubes. If the blending of oils causes the precipitation of asphaltenes, the oils are said to be incompatible as opposed to compatible oils that do not precipitate asphaltenes on blending. Thus, incompatible blends of oils have a much greater tendency for fouling and coking than compatible oils. If a blend of two or more oils have some proportion of the oils that precipitate asphaltenes, the set of oils are said to be potentially incompatible. Fortunately, most blends of unprocessed crude oils are not potentially incompatible. It is only for that reason that many refineries can process petroleum crudes for long times without the need to shut down and clean out foulant and coke. Several crude oils have even been identified that are self incompatible. That is they contain insoluble asphaltenes even without blending. Nevertheless, once an incompatible oil or blend of oils is obtained, the rapid fouling and coldng that results usually requires shutting down the refinery process in a short time. This results in a large economic debit because while the process equipment is cleaned, large volumes of oil cannot be processed.

Therefore, it is desirable to increase the solubility of the asphaltenes in the crude oil. This can be achieved by adding asphaltene dispersants to the crude oil.

SUMMARY OF THE INVENTION

The present invention is an asphaltene dispersant containing an aromatic group, a sulfonic acid head group, and an alkyl tail containing 16 or more carbons and at least one branch of a methyl or longer alkyl. Preferably, the aromatic group is a fused two ring aromatic and the tail a branched two tail alkyl group of 30 carbons or longer. More preferably, the dispersant is a mixture with each alkyl tail varying from one to more than 30 carbons such that there are at least a total of 30 carbons in the tail and a branched methyl or longer branch for every 12 carbons in the tail. Thus, these asphaltene dispersants need not be a pure compound but may be a mixture of compounds of the above description, such as prepared by reacting a petroleum derived aromatic stream and a mixture of olefins or alcohols in the presence of a Friedel Crafts catalyst, such as $AlCl_3$, followed by sulfonation of the aromatic.

These asphaltene dispersants are useful because their addition at low concentrations, one weight percent or less and preferably less than 1000 parts per million, solubilize asphaltenes in petroleum or petroleum derived oils to prevent asphaltenes from either precipitating or adsorbing on metal surfaces and thereby reducing their tendency to foul or coke metal surfaces, especially heated metal surfaces, such as heat exchanger and furnace tube metal surfaces.

BRIEF DESCRIPTION OF THE DRAWINGS

FIG. 1 shows a schematic diagram of the structure iso-$C_{15}$-$C_{15}$ naphthalene acid.

FIG. 2 shows a schematic diagram of a preferred asphaltene dispersant structure of the present invention.

DESCRIPTION OF THE PREFERRED EMBODIMENT

In the present invention it has been discovered that blending a member of a family of branched alkyl aromatic sulfonic acids is particularly effective at increasing the solubility of the asphaltenes in a petroleum derived oil. It is well known that alkyl benzene sulfonic acids are effective asphaltene dispersants (Chang and Fogler, Langmuir, 10, 1749–1757) and are being sold commercially for that purpose. However, both Chang and Fogler and we have found that these compounds with linear alkyl chain lengths above 16 carbons are not effective because of the lack of solubility in the oil. This led Chang and Fogler to conclude that the optimum alkyl chain length is 12 carbons. However, we have discovered that the reason for this lack of solubility is because the alkyl chains containing more than 16 carbons form wax-like crystals and promote their precipitation from the oil. This led us to alkyl chains containing branched methyls that interfere with crystal formation. The result was that branched alkyl aromatic sulfonic acids became increasingly better asphaltene dispersants as the alkyl chain length was increased, and much better than linear alkyl aromatic sulfonic acids. Then it was discovered that two tails of branched alkyl chains attached to aromatic sulfonic acids gave an additional boost in dispersant effectiveness. Finally, in comparing alkyl aromatic sulfonic acids of different size aromatic rings, we discovered that two fused aromatic rings are better dispersants than those containing one ring (benzene) or three fused rings. This leads us to conclude that the optimum alkyl aromatic sulfonic acid dispersant for asphaltenes is one that contains branched, two alkyl tails, a two fused ring aromatic, and a sulfonic acid head. FIG. 1 shows one with two tails of 15 carbons each and one methyl branch. The preferred dispersant would be a mixture of compounds with each tail varying from 1 to 15 carbons while the total number of carbons or sum of both tails, is 30 or more and with at least one methyl branch on each tail that is longer than 12 carbons. Thus, the preferred asphaltene dispersant is better defined by FIG. 2 where R and Q are alkyl tails joined to a carbon that is attached in any position on the naphthalene ring. R and Q are alkyl chains with at least one branched methyl or longer alkyl group for every 20 carbons, and $R+Q \geq 29$.

The asphaltene dispersants are particularly useful in an oil compatibility method which allows blending potentially incompatible petroleum oil. This method, which is described below, allows for determination of the effectiveness of a dispersant.

MEASUREMENT OF DISPERSANT EFFECTIVENESS

The Oil Compatibility Method is based upon tests with the individual oils involving blending with mixtures of a model solvent, toluene, and a model nonsolvent, n-heptane. The Oil Compatibility Method and tests provide us with a method to measure quickly the ability of a dispersant to increase the solubility of asphaltenes and to predict the improvement of the compatibility of any mixture of oils without the need for interpreting the results of thermal fouling tests. We measure the resulting increase in solubility of asphaltenes by the decrease in toluene equivalence, the percent toluene (asphaltene solvent) in heptane (asphaltene nonsolvent) required to keep asphaltenes in the oil in solution. This has enabled us to screen quickly the effectiveness of various synthetic and commercial additives as asphaltene dispersants.

OIL COMPATIBILITY METHOD

Two or more tests of each petroleum oil with a test liquid containing different proportions of a nonpolar asphaltene solvent and of a nonpolar asphaltene nonsolvent enables predicting if a given blend of oils are potentially incompatible. This is based upon determining the Insolubility Number and the Solubility Blending Number for each petroleum oil in the blend using the petroleum oil tests. Here we mean nonpolar when the molecular structure of the liquid only includes atoms of carbon, hydrogen, and sulfur. Once more, it has been learned that potentially incompatible oils can be processed with little fouling or coking as long as they are blended in the correct order, as predicted from the oil tests, and as long as certain proportions of the oils in the blend are avoided, as also are predicted by the Insolubility Number and the Solubility Blending Number of each oil in the blend as determined by the oil tests.

The first step in determining the Insolubility Number and the Solubility Blending Number for a petroleum oil is to establish if the petroleum oil contains n-heptane insoluble asphaltenes. This is accomplished by blending 1 volume of the oil with 5 volumes of n-heptane and determining if asphaltenes are insoluble. Any convenient method might be used. One possibility is to observe a drop of the blend of test liquid mixture and oil between a glass slide and a glass cover slip using transmitted light with an optical microscope at a magnification of from 50 to 600×. If the asphaltenes are in solution, few, if any, dark particles will be observed. If the asphaltenes are insoluble, many dark, usually brownish, particles, usually 0.5 to 10 microns in size, will be observed. Another possible method is to put a drop of the blend of test liquid mixture and oil on a piece of filter paper and let dry. If the asphaltenes are insoluble, a dark ring or circle will be seen about the center of the yellow-brown spot made by the oil. If the asphaltenes are soluble, the color of the spot made by the oil will be relatively uniform in color. If the petroleum oil is found to contain n-heptane insoluble asphaltenes, the procedure described in the next three paragraphs is followed for determining the Insolubility Number and the Solubility Blending Number. If the petroleum oil is found not to contain n-heptane insoluble asphaltenes, the Insolubility Number is assigned a value of zero and the Solubility Blending Number is determined by the procedure described in the section labeled, "Petroleum Oils without Asphaltenes."

Asphaltene Containing Petroleum Oils

The determination of the Insolubility Number and the Solubility Blending Number for a petroleum oil containing asphaltenes requires testing the solubility of the oil in test liquid mixtures at the minimum of two volume ratios of oil to test liquid mixture. The test liquid mixtures are prepared by mixing two liquids in various proportions. One liquid is nonpolar and a solvent for the asphaltenes in the oil while the other liquid is nonpolar and a nonsolvent for the asphaltenes in the oil. Since asphaltenes are defined as being insoluble in n-heptane and soluble in toluene, it is most convenient to select the same n-heptane as the nonsolvent for the test liquid and toluene as the solvent for the test liquid. Although the selection of many other test nonsolvents and test solvents can be made, there use provides not better definition of the preferred oil blending process than the use of n-heptane and toluene described here.

A convenient volume ratio of oil to test liquid mixture is selected for the first test, for instance, 1 ml. of oil to 5 ml. of test liquid mixture. Then various mixtures of the test liquid mixture are prepared by blending n-heptane and toluene in various known proportions. Each of these is mixed with the oil at the selected volume ratio of oil to test liquid mixture. Then it is determined for each of these if the asphaltenes are soluble or insoluble. Any convenient method might be used. One possibility is to observe a drop of the blend of test liquid mixture and oil between a glass slide and a glass cover slip using transmitted light with an optical microscope at a magnification of from 50 to 600×. If the asphaltenes are in solution, few, if any, dark particles will be observed. If the asphaltenes are insoluble, many dark, usually brownish, particles, usually 0.5 to 10 microns in size, will be observed. Another possible method is to put a drop of the blend of test liquid mixture and oil on a piece of filter paper and let dry. If the asphaltenes are insoluble, a dark ring or circle will be seen about the center of the yellow-brown spot made by the oil. If the asphaltenes are soluble, the color of the spot made by the oil will be relatively uniform in color. The results of blending oil with all of the test liquid mixtures are ordered according to increasing percent toluene in the test liquid mixture. The desired value will be between the minimum percent toluene that dissolves asphaltenes and the maximum percent toluene that precipitates asphaltenes. More test liquid mixtures are prepared with percent toluene in between these limits, blended with oil at the selected oil to test liquid mixture volume ratio, and determined if the asphaltenes are soluble or insoluble. The desired value will be between the minimum percent toluene that dissolves asphaltenes and the maximum percent toluene that precipitates asphaltenes. This process is continued until the desired value is determined within the desired accuracy. Finally, the desired value is taken to be the mean of the minimum percent toluene that dissolves asphaltenes and the maximum percent toluene that precipitates asphaltenes. This is the first datum point, $T_1$, at the selected oil to test liquid mixture volume ratio, $R_1$. This test is called the toluene equivalence test.

The second datum point can be determined by the same process as the first datum point, only by selecting a different oil to test liquid mixture volume ratio. Alternatively, a percent toluene below that determined for the first datum point can be selected and that test liquid mixture can be added to a known volume of oil until asphaltenes just begin to precipitate. At that point the volume ratio of oil to test liquid mixture, $R_2$, at the selected percent toluene in the test liquid mixture, $T_2$, becomes the second datum point. Since the accuracy of the final numbers increase as the further apart the second datum point is from the first datum point the preferred test liquid mixture for determining the second datum point is 0% toluene or 100% n-heptane. This test is called the heptane dilution test.

The Insolubility Number, $I_N$, is given by:

$$I_N = T_2 - \left[\frac{T_2 - T_1}{R_2 - R_1}\right] R_2$$

and the Solubility Blending Number, $S_{BN}$, is given by:

$$S_{BN} = I_N \left[1 + \frac{1}{R_2}\right] - \frac{T_2}{R_2}$$

Petroleum Oils Without Asphaltenes

If the petroleum oil contains no asphaltenes, the Insolubility number is zero. However, the determination of the Solubility Blending Number for a petroleum oil not containing asphaltenes requires using a test oil containing asphaltenes for which the Insolubility Number a nd the Solubility Blending Numbers have previously been determined, using the procedure just described First, 1 volume of the test oil is blended with 5 volumes of the petroleum oil. Insoluble asphaltenes may be detected by the microscope or spot technique, described above. If the oils are very viscous (greater than 100 centipoises), they may be heated to 100° C. during blending and then cooled to room temperature before looking for insoluble asphaltenes. Also, the spot test may be done on a blend of viscous oils in an oven at 50–70° C. If insoluble asphaltenes are detected, the petroleum oil is a nonsolvent for the test oil and the procedure in the next paragraph should be followed. However, if no insoluble asphaltenes are detected, the petroleum oil is a solvent for the test oil and the procedure in the paragraph following the next paragraph should be followed.

If insoluble asphaltenes were detected when blending 1 volume of the test oil with 5 volumes of the petroleum oil, small volume increments of the petroleum oil are added to 5 ml. of the test oil until insoluble asphaltenes are detected. The volume of nonsolvent oil, $V_{NSO}$, is equal to the average of the total volume of the petroleum oil added for the volume increment just before insoluble asphaltenes are detected and the total volume added when insoluble asphaltenes were first detected. The size of the volume increment may be reduced to that required for the desired accuracy. This is called the nonsolvent oil dilution test. If $S_{BNTO}$ is the Solubility Blending Number of the test oil and $I_{NTO}$ is the Insolubility Number of the test oil, then the Solubility Blending Number of the nonsolvent oil, $S_{BN}$, is given by:

$$S_{BN} = S_{BNTO} - \frac{5[S_{BNTO} - I_{NTO}]}{V_{NSO}}$$

If insoluble asphaltenes were not detected when blending 1 volume of the test oil with 5 volumes of the petroleum oil, the petroleum oil is a solvent oil for the test oil. The same oil to test liquid mixture volume ratio, $R_{TO}$, as was used to measure the Insolubility Number and Solubility Blending Number for the test oil is selected. However, now various mixtures of the test liquid are prepared by blending different known proportions of the petroleum oil and n-heptane instead of toluene and n-heptane. Each of these is mixed with the test oil at a volume ratio of oil to test liquid mixture equal to $R_{TO}$. Then it is determined for each of these if the asphaltenes are soluble or insoluble, such as by the microscope or the spot test methods discussed previously. The results of blending oil with all of the test liquid mixtures are ordered according to increasing percent petroleum oil in the test liquid mixture. The desired value will be between the minimum percent petroleum oil that dissolves asphaltenes and the maximum percent petroleum oil that precipitates asphaltenes. More test liquid mixtures are prepared with percent petroleum oil in between these limits, blended with the test oil at the selected test oil to test liquid mixture volume ratio ($R_{TO}$) and determined if the asphaltenes are soluble or insoluble. The desired value will be between the minimum percent petroleum oil that dissolves asphaltenes and the maximum percent petroleum oil that precipitates asphaltenes. This process is continued until the desired value is determined within the desired accuracy. Finally, the desired value is taken to be the mean of the minimum percent petroleum oil that dissolves asphaltenes and the maximum percent petroleum oil that precipitates asphaltenes. This is the datum point, Tso, at the selected test oil to test liquid mixture volume ratio, $R_{TO}$. This test is called the solvent oil equivalence test. If $T_{TO}$ is the datum point measured previously at test oil to test liquid mixture volume ratio, $R_{TO}$, on the test oil with test liquids composed of different ratios of toluene and n-heptane, then the Solubility Blending Number of the petroleum oil, $S_{BN}$, is given by:

$$S_{BN} = 100\left[\frac{T_{TO}}{T_{SO}}\right]$$

Mixtures of Petroleum Oils

Once the Solubility Blending Number is determined for each component the Solubility Blending Number for a mixture of oils, $S_{BNmix}$, is given by:

$$S_{BNmix} = \frac{V_1 S_{BN_1} + V_2 S_{BN_2} + V_3 S_{BN_3} + \ldots}{V_1 + V_2 + V_3 + \ldots}$$

where $V_1$ is the volume of component 1 in the mixture.

The criterion for compatibility for a mixture of petroleum oils is that the Solubility Blending Number of the mixture of oils is greater than the Insolubility Number of any component in the mixture. Therefore, a blend of oils is potentially incompatible if the Solubility Blending Number of any component oil in that blend is less than or equal to the Insolubility Number of any component in that blend. Once asphaltenes precipitate, it takes on the order of hours to weeks for the asphaltenes to redissolve while it takes of the order of minutes to process the oil in refinery equipment. Thus, to prevent fouling and coking a potentially incompatible blend of oils must be blended to always keep the Solubility Blending Number of the mixture higher than the Insolubility Number of any component in the blend. Thus, both the order of blending and the final proportions of oils in the blend are important If one starts with the oil of highest Solubility Blending Number and blends the remaining oils in the order of decreasing Solubility Blending Number and if the final mixture meets the compatibility criterion of the Solubility Blending Number of the mixture is greater than the Solubility Number of any component in the blend, then compatibility of the oils throughout the blending process is assured even though the blend of oils is potentially incompatible. The result is that the blend of oils will produce the minimum fouling and/or coking in subsequent processing.

EXAMPLE 1

The effect of 1 wt. % and 5 wt. % of alkyl benzene sulfonic acids on reduction of toluene equivalence of Baytown Cat Cracker Bottoms is shown below. While a $C_8$ tail reduced toluene equivalence (TE) for a short time, tails much longer than 12 carbons were required for the dispersion to last for as long as a day and exhibit long term stability. However, tails longer than 16 carbons resulted in a dispersant that was only partially soluble in the oil because the tails crystallized like a wax. A branched $C_{24}$ alkyl benzene sulfonic acid exhibited the best performance in terms of TE reduction and long term stability. In addition, the branched, 24 carbon tail benzene sulfonic acid used is an intermediate in the manufacture of lube oil detergents (Exxon Chemicals Paramins) and is named SA119.

a. $C_8$—1% reduced TE from 87 to 60, insoluble next day
     —5% reduced TE from 87 to 55, insoluble next day
  b. $C_{12}$—1% reduced TE from 87 to 60, insoluble next day
     —5% reduced TE from 87 to 55, soluble next day
  c. $C_{18}$—is a solid and partially soluble in toluene/heptane
  d. $IsoC_{24}$ (5 branched methyls)
     —1% reduced TE from 87 to 60, soluble next day
     —5% reduced TE from 87 to 55, soluble next day Thus, branched allyl benzene sulfonic acids are better than linear alkyl benzene sulfonic acids as asphaltene dispersants in crude oil.

EXAMPLE 2

Table 1 contains the results of 25 synthesized dispersants. The synthesis involved alkylation of an aromatic ring, followed by sulfonation. The variables in the synthesis are the type of aromatic and the type of olefin used for alkylation. Alpha olefins give a single tail while internal olefins give two tails with a distribution of splits of the total chain length between the two tails. In addition, the total number of carbons and the degree of branching of the olefins was varied. $^{13}C$ NMR was used to measure the chain length, methyl branches per molecule, percent of olefin sample that was olefin, and the percent of aromatics that was functionalized by the addition of an olefin. Elemental analysis was used to determine the percent sulfonation. Finally, reduction in the toluene equivalence of Maya crude oil after the addition of 5% dispersant was used to measure the effectiveness as an asphaltene dispersant. Results in Table 1 illustrate the salient features of our invention.

(a) In comparing Entries 3, 16, and 23 with the same alpha olefin, the dispersant with naphthalene results in a lower toluene equivalence than with toluene or with phenanthrene. In addition, in comparing 7 and 8 with 24 or 9 with 25, naphthalene gives better results than phenanthrene.

(b) In comparing Entry 20 and 21 with 14 or Entry 19 with 1, it is clear that naphthalene a two fused aromatic ring structure is a superior performer compared to two aromatic rings that are connected by a C-C bond (binaphthyl) or tetralin where one ring is aromatic and the other nonaromatic.

(c) Since the best dispersants were prepared with internal olefins, two tails are more effective than single tails.

(d) Since the longest chain length internal olefins produced the best dispersants as seen by 7, 8, 10 and 11 with carbon chains of 37 to 47 on naphthalene, the alkyl tails of at least 30 carbons are most effective.

(e) In comparing 12 and 14, one sees that the more branched tail produces a better dispersant even with a low degree of functionalization.

TABLE 1

Example Synthetic Asphaltene Dispersants

| Toluene No. | Aromatic Equivalence | Olefin Internal or Alpha ? | Carbon Chain Length | Methyls per Molecule | % Functionalization | Maya |
|---|---|---|---|---|---|---|
| 1 | Toluene | Internal | 23 | 0.15 | 119 | 34 |
| 2 | Toluene | Internal | 23 | 0.15 | 78 | 31 |
| 3 | Toluene | Alpha | 21 | 0 | 76 | 34 |
| 4 | Toluene | Internal | [20–24] | [0.33] | 78 | 32 |
| 5 | Toluene | Internal | 25 | 0 | 36 | 32 |
| 6 | Toluene | Internal | 33 | 0.99 | 37 | 23.5 |
| 7 | Naphthalene | Internal | 37 | 0.33 | 29 | 13 |
| 8 | Naphthalene | Internal | 37 | 0.33 | 114 | 11 |
| 9 | Naphthalene | Internal | 33 | 0.99 | 44 | 17 |
| 10 | Naphthalene | Internal | 47 | 0.28 | 85 | 11 |
| 11 | Naphthalene | Internal | 37 | 0.54 | 90 | 13 |
| 12 | Naphthalene | Internal | 25 | 1.9 | 51 | 17 |
| 13 | Naphthalene | Internal | 18 | 0.10 | 95 | 31 |
| 14 | Naphthalene | Internal | 23 | 0.15 | 89 | 23 |
| 15 | Naphthalene | Internal | 18 | 0.17 | 65 | 32 |
| 16 | Naphthalene | Alpha | 21 | 0 | 86 | 28 |
| 17 | Naphthalene | Internal | 29 | 0.33 | 60 | 32 |
| 18 | Naphthalene | Alpha | 17 | 0.04 | 40 | 26 |
| 19 | Tetralin | Internal | 37 | 0.33 | 76 | >36 |
| 20 | Tetralin | Internal | 23 | 0.15 | 103 | 29 |
| 21 | Binaphthyl | Internal | 23 | 0.15 | 119 | >30 |
| 22 | Phenanthrene | Internal | 23 | 0.15 | 62 | 30 |
| 23 | Phenanthrene | Alpha | 21 | 0 | 34 | 34 |
| 24 | Phenanthrene | Internal | 37 | 0.33 | 43 | 26.5 |
| 25 | Phenanthrene | Internal | 33 | 0.99 | 62 | 29 |

What is claimed is:

1. An asphaltene dispersant composition comprising an aromatic, a sulfonic acid head, and one or more alkyl tails including at least 16 carbons and at least one branch of an alkyl group.

2. The composition of claim 1 wherein said aromatic is two fused rings.

3. The composition of claim 1 wherein said tail is a two branched alkyl tail of at least 30 carbon atoms.

4. The composition of claim 3 wherein each branch of said alkyl tail includes an alkyl branch for every 20 carbon atoms.

5. The composition of claim 3 wherein each branch of said alkyl tail includes an alkyl branch for every 12 carbon atoms.

6. The composition of claim 1 wherein said alkyl group is a methyl group.

7. A method to disperse asphaltenes in a petroleum derived oil comprising adding to said oil 10 to 1000 ppm of an alkyl aromatic sulfonic acid compound including an aromatic, a sulfonic acid head, and one or more alkyl tails including at least 16 carbons and at least one branch of an alkyl group.

* * * * *